US011617917B2

(12) United States Patent
Mankodi et al.

(10) Patent No.: US 11,617,917 B2
(45) Date of Patent: Apr. 4, 2023

(54) NON-LINEAR BREATH ENTRAINMENT

(71) Applicant: BOSE CORPORATION, Framingham, MA (US)

(72) Inventors: Harsh A. Mankodi, Brighton, MA (US); David Rolland Crist, Watertown, MA (US); Christopher R. Paetsch, Cambridge, MA (US); Joseph Rossi, Jamaica Plain, MA (US); Sara Adkins, Allston, MA (US); Chia-Ling Li, Framingham, MA (US); Navaneethan Siva, Waltham, MA (US); Kathleen Elizabeth Kremer, Southborough, MA (US); Alexander de Raadt St James, Revere, MA (US); Jeffrey Miller, North Reading, MA (US); Connor Rog, Cumberland, ME (US); Stephen A. McDonald, Northborough, MA (US); Paul Naddaff, Newton, MA (US); John Andrew Trotter, Sudbury, MA (US); Victoria A. Grace, Framingham, MA (US)

(73) Assignee: BOSE CORPORATION, Framingham, MA (US)

( * ) Notice: Subject to any disclaimer, the term of this patent is extended or adjusted under 35 U.S.C. 154(b) by 421 days.

(21) Appl. No.: 16/735,057

(22) Filed: Jan. 6, 2020

(65) Prior Publication Data
US 2020/0215383 A1 Jul. 9, 2020

Related U.S. Application Data

(60) Provisional application No. 62/789,343, filed on Jan. 7, 2019.

(51) Int. Cl.
*G09B 19/00* (2006.01)
*A63B 23/02* (2006.01)
(Continued)

(52) U.S. Cl.
CPC ........ *A63B 23/0244* (2013.01); *A61B 5/0816* (2013.01); *A61B 5/7264* (2013.01); *G09B 19/00* (2013.01)

(58) Field of Classification Search
CPC .. G09B 19/00; G09B 19/003; A63B 23/0244; A61B 5/0816
See application file for complete search history.

(56) References Cited

U.S. PATENT DOCUMENTS

2005/0124906 A1* 6/2005 Childre ............... A61B 5/0816
600/529
2006/0102171 A1 5/2006 Gavish
(Continued)

FOREIGN PATENT DOCUMENTS

EP 0 856 334 A2 8/1998

OTHER PUBLICATIONS

International Search Report and Written Opinion for International Application No. PCT/US2020/012349 dated Apr. 15, 2020.

*Primary Examiner* — Peter R Egloff
(74) *Attorney, Agent, or Firm* — Patterson + Sheridan, LLP

(57) ABSTRACT

Aspects of the present disclosure provide methods, apparatuses, and systems for non-linear breathing entrainment. As described herein, "breathing entrainment" refers to guiding a user's breath or breathing. According to an aspect, an initial breathing period and a final breathing period are selected. Based on the initial and final breathing periods, a non-linear breath rate per minute sequence is determined. A guiding stimulus is output and aligned with the non-linear breath rate per minute sequence. The guiding stimulus is non-linearly altered with the non-linear breath rate per minute sequence to align with the final breathing period over an interval of time. The non-linear alterations of the guiding (Continued)

stimulus vary based on an amount of time the guiding stimulus has been output.

20 Claims, 3 Drawing Sheets

(51) Int. Cl.
*A61B 5/08* (2006.01)
*A61B 5/00* (2006.01)

(56) References Cited

U.S. PATENT DOCUMENTS

| | | | |
|---|---|---|---|
| 2008/0305463 A1* | 12/2008 | Ichikawa | G09B 19/00 434/257 |
| 2009/0024047 A1 | 1/2009 | Shipley et al. | |
| 2009/0263773 A1* | 10/2009 | Kotlyar | G09B 19/003 715/764 |
| 2011/0306024 A1* | 12/2011 | Furuta | G09B 19/00 434/258 |
| 2014/0178844 A1* | 6/2014 | Warren | G09B 19/003 434/247 |
| 2016/0151603 A1* | 6/2016 | Shouldice | A61B 5/486 600/26 |
| 2016/0314698 A1* | 10/2016 | Saada | G09B 19/00 |
| 2017/0173298 A1 | 6/2017 | Benway et al. | |
| 2017/0358239 A1* | 12/2017 | Arney | A61B 5/0205 |
| 2017/0358240 A1* | 12/2017 | Blahnik | G09B 5/06 |
| 2018/0014741 A1* | 1/2018 | Chou | A61B 5/6803 |
| 2018/0272189 A1* | 9/2018 | Lee | G06F 3/011 |

* cited by examiner

NON-LINEAR BREATH ENTRAINMENT

CROSS REFERENCE TO RELATED APPLICATIONS

This application claims priority to and benefit of U.S. Provisional Patent Application No. 62/789,343, filed Jan. 7, 2019, the contents of which are herein incorporated by reference in its entirety.

FIELD

Aspects of the present disclosure generally relate to methods, apparatuses, and systems for non-linear breathing entrainment.

BACKGROUND

Utilizing breathing entrainment to regulate a user or subject's breathing rate, or amount of breaths taken per minute, can be beneficial in a number of health fields. For example, breathing entrainment can be used in several clinical applications, potentially leading to more effective or quicker treatments of conditions, including: asthma, stress, anxiety, insomnia, panic disorder, recurrent abdominal pain, chronic obstructive pulmonary disease, chronic hyperventilation, hypertension, and congestive heart failure, among others. Breathing entrainment may also be utilized to assist people in falling asleep and for meditation or relaxation purposes.

Typical breath entrainment schemes modulate a user's actual breath rate in breaths per minute. In certain cases, a target rate is provided as a steady stimulus for the entire duration of the entrainment scheme. This involves effort by the user, as the user has to manage their breathing to match that stimulus. Another breath entrainment scheme decreases a user's amount of breaths per minute in a linear or step-wise manner by reducing the amount of breaths taken per minute by one full breath. For instance, if a user follows the breathing entrainment sequence for one minute taking 9 breaths per minute, the next reduction is to 8 breaths per minute, and so on. This type of breathing entrainment sequence may be uncomfortable for some users, being too unnatural and difficult to follow. Additionally, if a user fails to follow or accurately keep up with the breathing entrainment sequence, it can be difficult for the user to catch back up to the quick pace of the sequence. Therefore, there is a need for a breathing entrainment method that is easier for users to follow and complete.

SUMMARY

Aspects of the present disclosure provide methods, apparatuses, and systems for non-linear breathing entrainment. As described herein, "entrainment" and "breathing entrainment" each refer to guiding a user's breath or breathing. According to an aspect, an initial breathing period and a final breathing period are selected. Based on the initial and final breathing periods, a non-linear breath rate per minute sequence is determined. A guiding stimulus is output and aligned with the non-linear breath rate per minute sequence. The guiding stimulus is non-linearly altered with the non-linear breath rate per minute sequence to align with the final breathing period over an interval of time. The non-linear alterations of the guiding stimulus vary based on an amount of time the guiding stimulus has been output.

In an aspect, a method for breathing entrainment comprises selecting an initial breathing period. A breathing period is an amount of time from a beginning of one inhale to an end of a next exhale. The method further comprises selecting a final breathing period. The final breathing period is greater than the initial breathing period. The method further comprises outputting a guiding stimulus to a user, aligning the guiding stimulus with the initial breathing period, and non-linearly altering the guiding stimulus to align with the final breathing period over an interval of time. The non-linear alterations of the guiding stimulus vary based on an amount of time the guiding stimulus has been output.

The non-linear alterations of the guiding stimulus may further vary based on an estimation of a current breathing pattern of the user. The current breathing pattern of the user may be estimated using a biometric sensor. Non-linearly altering the guiding stimulus to align with the final breathing period may comprise time-stretching the guiding stimulus. The guiding stimulus may be one of a pre-produced sound, a pre-produced soundtrack, or dynamically generated. The final breathing period may be one of preset, user-selected, or based on input collected using at least one biometric sensor. The initial breathing period may be user-selected.

In another aspect, a wearable audio device comprises at least one speaker configured to output a guiding stimulus to a user and a processor. The processor is configured to select an initial breathing period. A breathing period is an amount of time from a beginning of one inhale to an end of a next exhale. The processor is further configured to select a final breathing period. The final breathing period is greater than the initial breathing period. The processor is further configured to align the guiding stimulus with the initial breathing period and non-linearly alter the guiding stimulus to align with the final breathing period over an interval of time. The non-linear alterations of the guiding stimulus vary based on an amount of time the guiding stimulus has been output.

The non-linear alterations of the guiding stimulus may further vary based on an estimation of a current breathing pattern of the user. The current breathing pattern of the user may be estimated using a biometric sensor. Non-linearly altering the guiding stimulus to align with the final breathing period may comprise time-stretching the guiding stimulus. The guiding stimulus may be one of a pre-produced sound, pre-produced soundtrack, or dynamically generated. The final breathing period may be one of preset, user-selected, or based on input collected using at least one biometric sensor. The initial breathing period may be user-selected.

In yet another aspect, an audio system comprises at least one speaker configured to output a guiding stimulus to a user and a processor. The processor is configured to select an initial breathing period. A breathing period is an amount of time from a beginning of one inhale to an end of a next exhale. The processor is further configured to select a final breathing period. The final breathing period is greater than the initial breathing period. The processor is further configured to align the guiding stimulus with the initial breathing period and non-linearly alter the guiding stimulus to align with the final breathing period over an interval of time. The non-linear alterations of the guiding stimulus vary based on an amount of time the guiding stimulus has been output.

The non-linear alterations of the guiding stimulus may further vary based on an estimation of a current breathing pattern of the user. The current breathing pattern of the user may be estimated using a biometric sensor. Non-linearly altering the guiding stimulus to align with the final breathing period may comprise time-stretching the guiding stimulus. The guiding stimulus may be one of a pre-produced sound, pre-produced soundtrack, or dynamically generated. The final breathing period may one of preset, user-selected, or based on input collected using at least one biometric sensor. The initial breathing period may be user-selected.

All examples and features mentioned herein can be combined in any technically possible manner.

DETAILED DESCRIPTION

Figure 1:
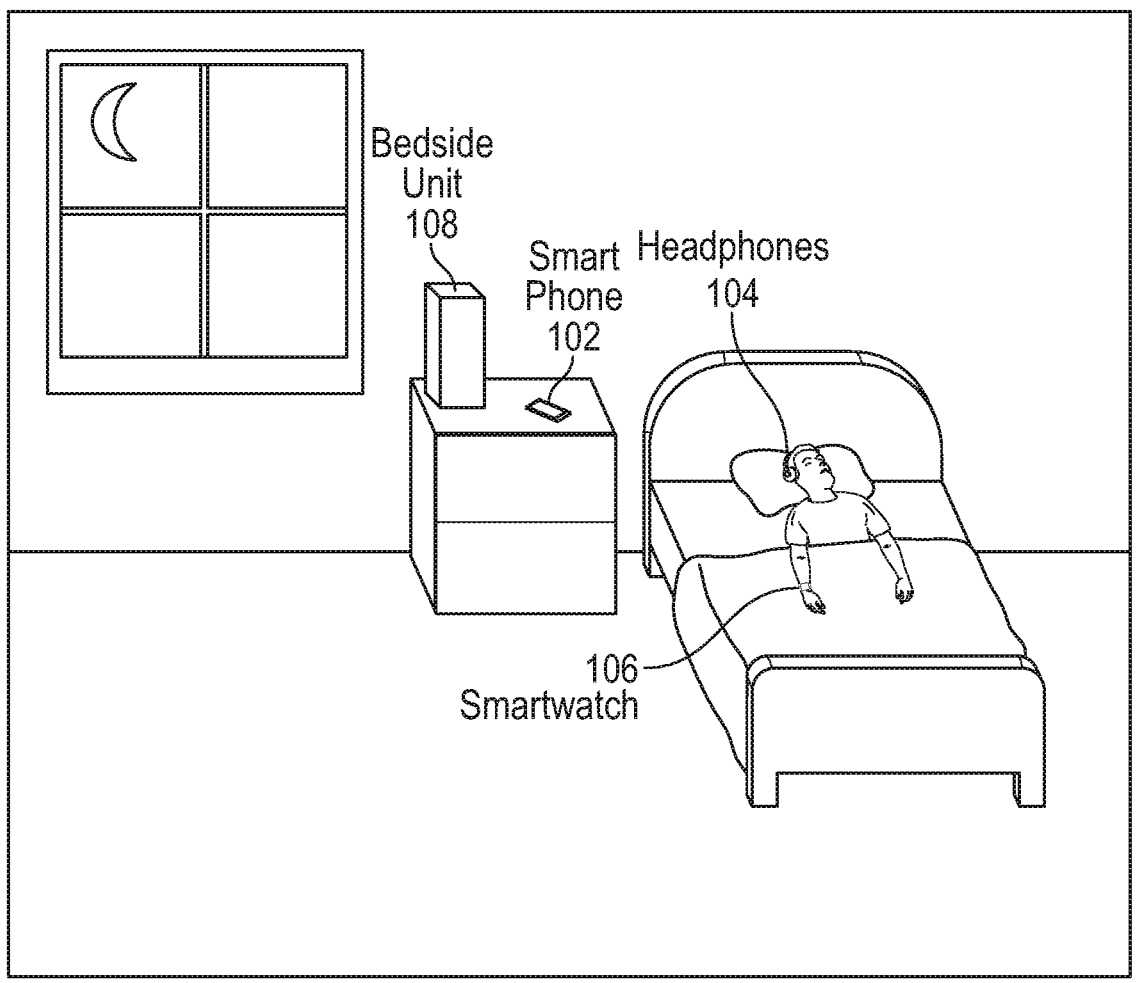
FIG. 1 illustrates an example audio system in a sleeping environment.

FIG. 1 illustrates an example audio system 100 in a sleeping environment, according to an aspect. The audio system 100 may be used to non-linearly alter a guiding stimulus from an initial breathing period to a final breathing period for non-linear breath entrainment. As described herein, "breath entrainment" refers to guiding a user's breath or breathing. Accordingly, the audio system 100 may be used to non-linearly alter a guiding stimulus from an initial breathing period to a final breathing period to guide a user's breath or breathing.

The audio system 100 includes headphones 104 and a smartwatch 106, which are shown as being worn by a subject or user. A headphone 104 refers to a device that fits around, on, or in an ear and that radiates acoustic energy into the ear canal. Headphones 104 are sometimes referred to as earphones, earpieces, headsets, earbuds, or sport headphones, and can be wired or wireless. The headphones 104 may comprise one or more of: a processing unit, a transceiver, one or more biosensors, one or more speakers, and one or more microphones. The headphones 104 may comprise an interface configured to receive input from a subject or user. A smartwatch 106 may be any type of wearable computer designed to be worn on a wrist of a subject or user, such as a fitness tracker. The smartwatch 106 may comprise one or more of: a processing unit, a transceiver, one or more biosensors, one or more speakers, and one or more microphones. The smartwatch 106 may comprise an interface configured to receive input from a subject or user.

The audio system 100 further includes a bedside unit 108 and a smartphone 102. The smartphone 102 may be a mobile phone, tablet, phablet, or laptop computer. The smartphone 102 may comprise one or more of: a processing unit, a transceiver, one or more biosensors, one or more speakers, and one or more microphones. The smartphone 102 may comprise an interface configured to receive input from a subject or user. The bedside unit 108 may be a stationary smart device, such as a smart speaker. The bedside unit 108 may have any shape and size capable of fitting on a surface in the sleeping environment, such as a dresser, desk, or night table. The bedside unit 108 may comprise one or more of: a processing unit, a transceiver, one or more biosensors, one or more speakers, and one or more microphones. In one embodiment, the bedside unit 108 comprises one or more contactless biosensors, such as a radio frequency (RF) sensor, a radar sensor, or an under-bed accelerometer and/or microphone. The bedside unit 108 may comprise an interface configured to receive input from a subject or user.

The headphones 104, the smartwatch 106, the bedside unit 108, and the smartphone 102 may each include any wired or wireless communication means suitable for use with any other device 102-108 disposed in the sleeping environment, such as WiFi, Bluetooth, Near Field Communications (NFC), USB, micro USB, or any suitable wired or wireless communications technologies known to one of ordinary skill in the art. For example, the headphones 104 may comprise one or more speakers while the bedside unit 108 comprises one or more biosensors in communication with the one or more speakers of the headphones 104. Furthermore, the audio system 100 may include one or more of the devices 102-108, and is not required to include each device 102-108 shown. Thus, each device 102-108 in the audio system 100 may be optionally included, and only one device 102-108 is needed for non-linear breath entrainment.

The devices 102-108 of the audio system 100, either alone or in combination, are configured to: select an initial breathing period, select a final breathing period, the final breathing period being greater than the initial breathing period, output a guiding stimulus to a user, align the guiding stimulus with the initial breathing period, and non-linearly alter the guiding stimulus to align with the final breathing period over an interval of time, the non-linear alterations of the guiding stimulus varying based on an amount of time the guiding stimulus has been output.

Figure 2:
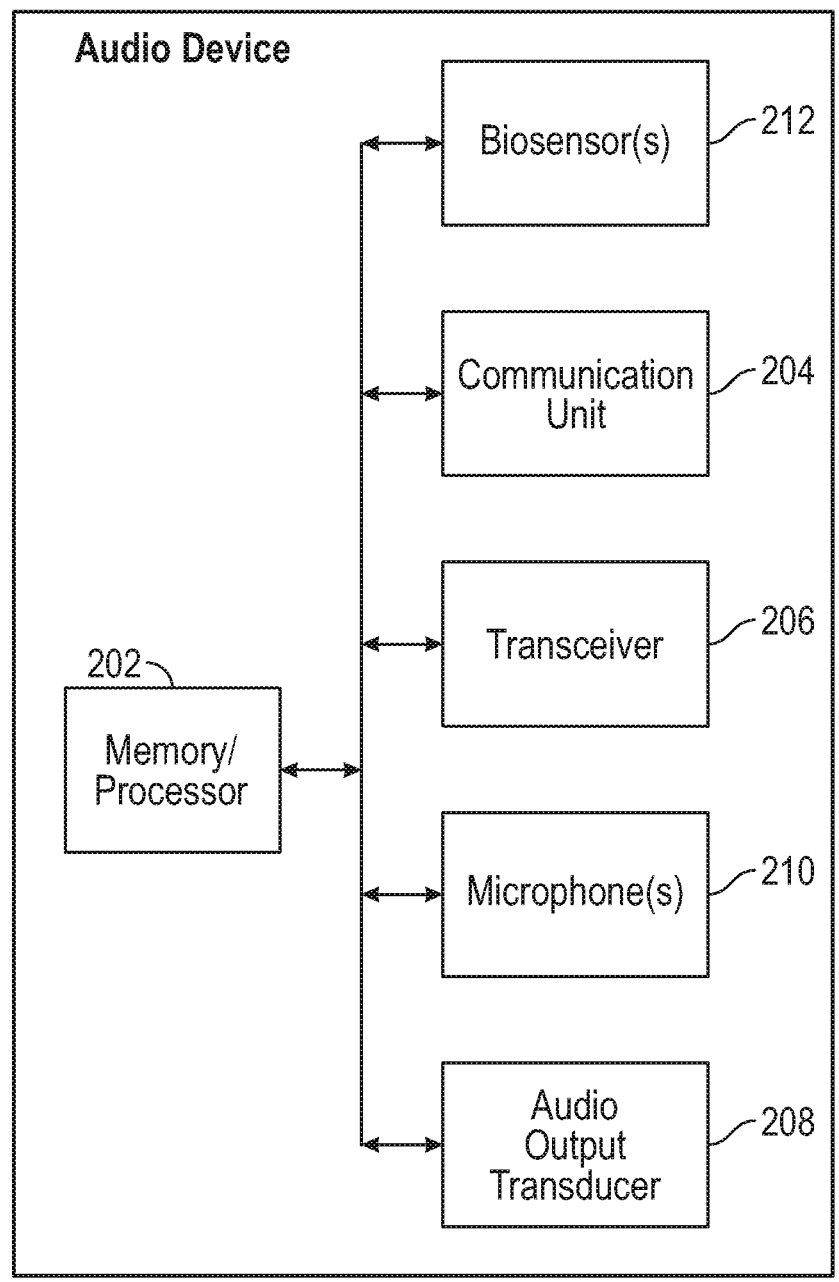
FIG. 2 illustrates example components of an audio device.

FIG. 2 illustrates example components of an audio device 200, in accordance with certain aspects of the present disclosure. According to an example, the audio device 200 is a wireless wearable audio device. The audio device 200 may be used in an audio system, such as the audio system 100 of FIG. 1. For instance, the audio device 200 may be any device 102-108 in the audio system 100 of FIG. 1. In one example, the audio device 200 is the headphones 104 of FIG. 1. In another example, the audio device 200 is the bedside unit 108 of FIG. 1. The audio device 200 may be used to non-linearly alter a guiding stimulus from an initial breathing period to a final breathing period for non-linear breath entrainment.

The audio device 200 includes a memory and processor 202, communication unit 204, a transceiver 206, a biosensor 212, and an audio output transducer or speaker 208. The memory may include Read Only Memory (ROM), a Random Access Memory (RAM), and/or a flash ROM. The memory stores program code for controlling the memory and processor 202. The memory and processor 202 control the operations of the audio device 200. Any or all of the components in FIG. 3 may be combined into multi-function components.

The processor 202 controls the general operation of the audio device 200. For example, the processor 202 performs process and control for audio and/or data communication. The processor 202 is configured to measure, receive, calculate, or detect at least one biosignal parameter of the subject. In combination with the audio output transducer 208, the processor 202 is configured to output a guiding stimulus. The processor 202 is further configured to alter the guiding stimulus. The processor 202 may be further configured to receive input from a subject or user, such as input regarding an initial breath rate per minute and a final breath rate per minute. In at least one example, the processor 202 is disposed on another device in an audio system, such as a smartphone, and is in communication with the audio device 200.

The communication unit 204 facilitates a wireless connection with one or more other wireless devices, such as with other devices in an audio system. For example, the communication unit 204 may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The audio device 200 may receive audio files wirelessly via the communication unit 204. Additionally or alternatively, the communication unit 204 may receive information associated with a subject's biosignal parameters, obtained via a contactless sensor. Examples of contactless sensors include a radio frequency (RF) sensor, a radar sensor, or an under-bed accelerometer.

The transceiver 206 transmits and receives information via one or more antennae to exchange information with one or more other wireless devices. The transceiver 206 may be used to communicate with other devices in an audio system, such as a bedside unit, a smartphone, and/or a smartwatch. The transceiver 206 is not necessarily a distinct component.

The audio device 200 includes the audio output transducer 208, which may be also known as a driver or speaker. In some examples, more than one output transducer 208 is used. The transducer 208 (that may be part of a microphone) converts electrical signals into sound and converts sound into electrical signals. The transducer 208 is configured to output a guiding stimulus to a user or subject. The transducer 208 outputs audio signals, including adjusted audio signals in an effort to regulate a user's breathing. For example, the transducer 208 may be configured to adjust audio signals in response to a subject's biosignal parameters. In at least one example, the transducer 208 is disposed on another device in an audio system, such as a bedside unit, and is in communication with the audio device 200.

The audio device 200 optionally includes one or more microphones 210. In an aspect, the microphones 210 are used to convert noises into electrical signals. In at least one example, one or more microphones 210 are disposed on another device in an audio system, such as a bedside unit, and are in communication with the audio device 200. The microphone 210 may be used to approximate or measure a user's breath rate per minute.

The audio device 200 optionally includes one or more biosensors 212 used to determine, sense, measure, monitor, or calculate a biosignal parameter of a subject wearing the audio device 200.

According to an aspect when the audio device 200 is headphones, only one earpiece (ear tip, ear cup) of the audio device 200 includes the biosensor 212. In an aspect, neither earpiece includes a biosensor 212. Instead, a biosensor 212, not on the audio device 200, may remotely detect a biosignal parameter of the subject. In an example, the biosensor 212 detects a subject's heartrate or heart rate variability (HRV) with a sensor disposed on the wrist, such as by utilizing a smartwatch. In an example, the biosensor 212 may be a contactless biosensor. The contactless biosensor is configured to report detected biosignal parameters to the processor 202, for example, via the communication unit 204. In at least one example, the biosensor 212 is disposed on another device in an audio system, such as a smartwatch, and is in communication with the audio device 200.

FIG. 2 illustrates communication between certain modules of an example audio device 200; however, aspects of the disclosure are not limited to the specific illustrated example. According to aspects, any module 202-212 is configured to communicate with any other module in the audio device 200. In one example, all modules 202-212 are connected to and communicate with each other.

Figure 3:
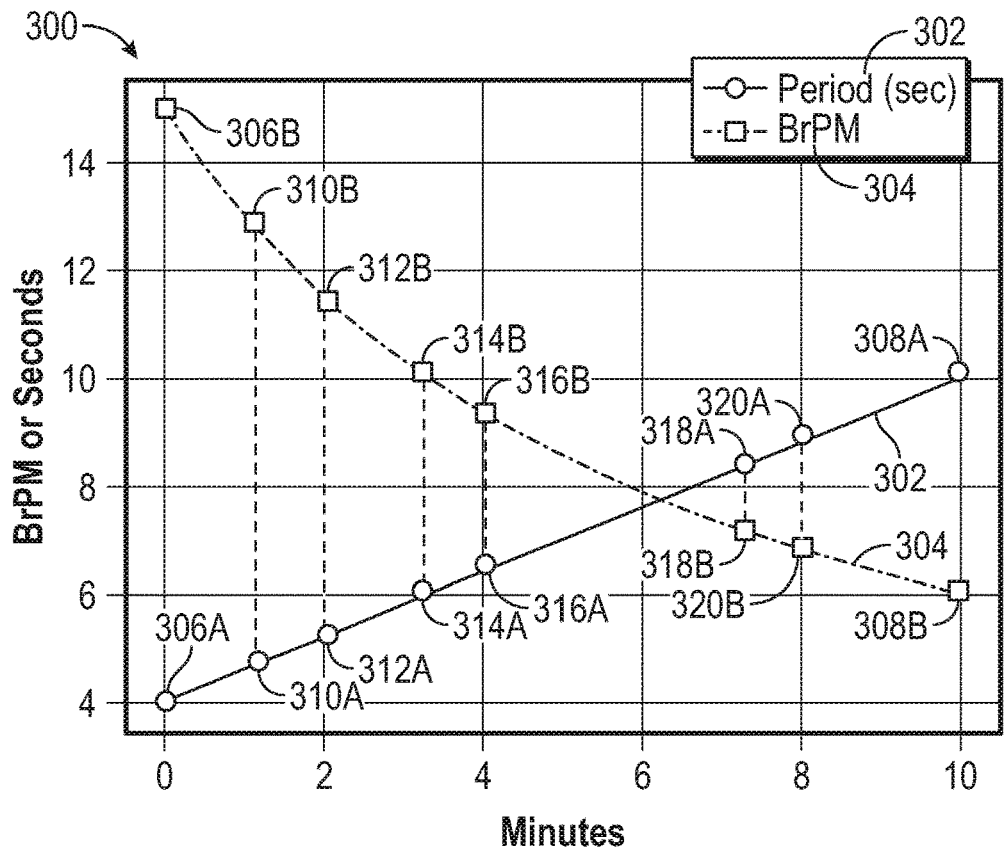
FIG. 3 illustrates an example graph of non-linear breathing entrainment.

FIG. 3 illustrates an example graph 300 for non-linear breathing entrainment, according to one embodiment. The data presented in graph 300 may be obtained using the audio system 100 of FIG. 1 and/or the audio device 200 of FIG. 2. The graph 300 comprises several points 310A-320B, which will be discussed below with reference to FIG. 4.

In the graph 300 of FIG. 3, a breathing period line 302 illustrates a breathing period increasing linearly. A breathing period is an amount of time from a beginning of one inhale to an end of a next exhale. For the breathing period line 302, the y-axis is seconds and the x-axis is minutes of entrainment. The breathing period line 302 is a straight line governed by Equation 1:

$$\text{Period} = \alpha * t + \text{Period}_{Initial} \qquad \text{Equation 1}$$

In equation 1, $\alpha$ is the slope, t is time in minutes, and $\text{Period}_{Initial}$ is the initial breathing period. Thus, since the breathing period line 302 is a straight line, the slope ($\alpha$) of the breathing period line 302 is seconds of period rise per minute of entrainment. The initial breathing period is illustrated by point 306A. As shown in the graph 300, the initial breathing period 306A is selected to be about 4 seconds (i.e., the amount of time between the beginning of one inhale to the end of a next exhale is about 4 seconds).

The initial breathing period 306A may be determined based on feedback from a biosensor, such as the biosensor 212 of FIG. 2. In such an embodiment, the biosensor may be configured to measure the user's respiration. The biosensor may further be configured to detect whether the user is inhaling and exhaling. The initial breathing period depends on the measured respiration. If a biosensor is used to determine the initial breathing period 306A, the initial entrainment breathing rate or period 306A may depend on the sensor data. For example, if a user's initial breathing rate is measured to be about 13 breaths per minute, the entrainment may begin at 12 breaths per minute, 1 breath per minute below the user's measured rate. In another example, the initial entrainment period may be a factor or fraction of the user's initial breathing period 306A. Further, there may be upper and/or lower limits to where the entrainment may begin, regardless of where the user's breathing period is measured. The initial breathing period 306A may also be selected by a subject or user, or may be preset or predetermined.

The breathing period line 304 may end at the conclusion of the entrainment sequence at a final breathing period point 308A. A final breathing period 308A is the desired breathing period after the breathing entrainment has been completed. Thus, the slope of the breathing period line 304 is calculated based on the initial breathing period 306A and the final breathing period 308A such that the breathing period line 304 linearly extends from the initial breathing period 306A to the final breathing period 308A. The final breathing period 308A may be selected by a subject or user, may be prescribed (preset or predetermined), or may be determined by at least one biosensor, such as the biosensors 212 of FIG. 2. If the final breathing period is prescribed, the entrainment may converge towards approximately 6 breaths per minute (10 second periods). In aspects, approximately 6 breaths per minute (10 second periods) maximizes relaxation and likelihood of sleep onset for most people. Biosensors that provide information about Heart Rate (HR) and/or HRV help set the target rate such that HRV is high (ideally, maximized) through the phenomenon well-documented in literature known as Respiratory Sinus Arrhythmia (RSA). The rate at which the HRV is maximized is called the Resonance Frequency, which can vary person-to-person. Setting target HRV to the Resonance Frequency enhances effectiveness of the entrainment experience through personalization.

In the graph 300, the final breathing period 308A is selected to be about 10 seconds (i.e., the amount of time between the beginning of one inhale to the end of a next exhale is about 10 seconds). Once both the initial breathing period 306A and the final breathing period 308A are determined, the slope of the breathing period line 304 is calculated.

In the graph 300, a breath rate per minute (BrPM) line 304 illustrates a breath rate per minute of a user decreasing non-linearly (i.e., in a non-linear decay). A breath rate per minute is the amount of breaths a subject takes in one minute. For the BrPM line 304, the y-axis is breaths per minute and the x-axis is minutes of entrainment. The breath rate per minute line 304 is the inverse of the breathing period line 302. In other words, the non-linear breath rate per minute line 304 is governed by Equation 2:

$$Rate_{Breath} = \frac{60 \text{ seconds}}{Period} \quad \text{Equation 2}$$

The BrPM line 304 begins at an initial BrPM point 306B and extends to a target or final BrPM point 308B. The initial BrPM 306B is the user's initial BrPM when starting the entrainment. The initial BrPM 306B corresponds to the initial breathing period 306A. Thus, the initial BrPM 306B is selected to be about 14.5 breaths per minute, corresponding to a 4 second breathing period. The final BrPM 308B corresponds to the final breathing period 308A. As such, in the graph 300, the final BrPM 308B is selected to be about 6 breaths per minute, corresponding to a 10 second breathing period.

Both the initial BrPM 306B and the final BrPM 308B may individually be selected by a subject or user, or may individually be preset or predetermined. A user may select either an initial BrPM or an initial breathing period, and the other may automatically be calculated or populated to correspond. Thus, the user need not select both the initial BrPM and the initial breathing period. Similarly, the user may select either a final BrPM or a final breathing period, and the other may automatically calculate or populate to correspond so that the user need not select both the final BrPM and the final breathing period. If one or more of the initial BrPM, the final BrPM, the initial breathing period, or the final breathing period are preset or predetermined, the corresponding parameter will be automatically preset or predetermined as well.

Figure 4:
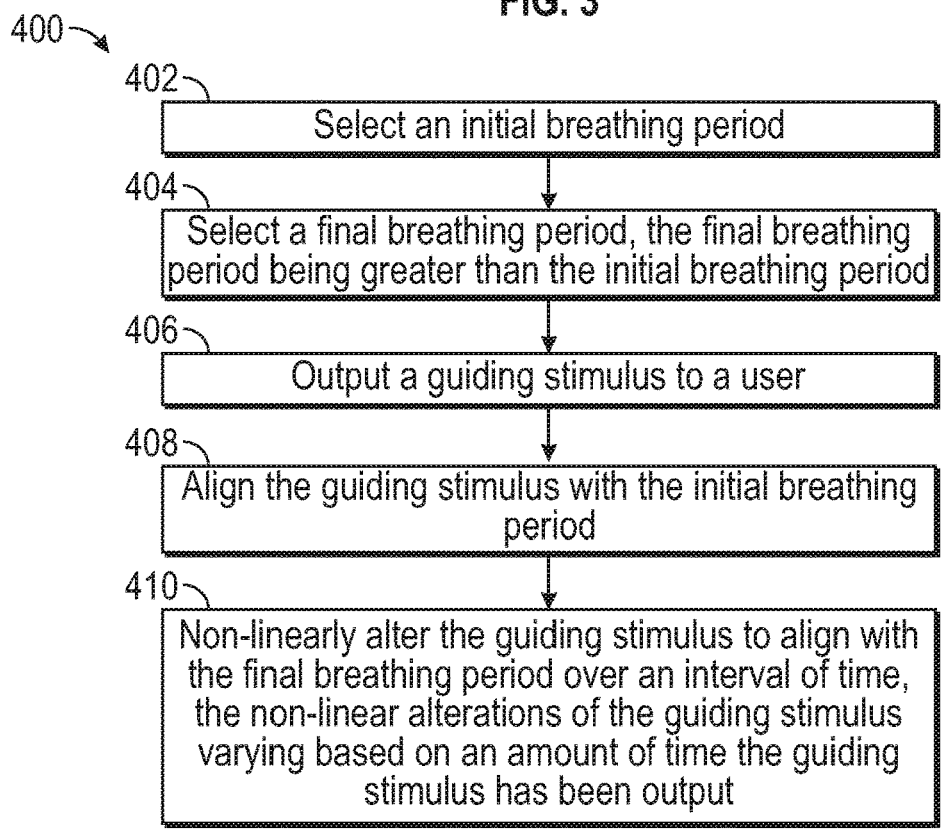
FIG. 4 illustrates an example method for non-linear breathing entrainment.

FIG. 4 illustrates an example method 400 for non-linear breathing entrainment, according to one embodiment. Method 400 may be implemented utilizing the audio system 100 of FIG. 1 and/or the audio device 200 of FIG. 2. For clarity, method 400 is described with reference to the graph 300 of FIG. 3.

In 402, an initial breathing period 306A is selected. A breathing period is an amount of time from a beginning of one inhale to an end of a next exhale. The initial breathing period 306A may be selected by a user or subject, or may be preset or predetermined. As shown in the graph 300, the initial breathing period 306A is selected to be about 4 seconds, corresponding to an initial BrPM 306B of about 14.5 breaths per minute. Another example of an initial breathing period may be about a 6 second breathing period or about 10 breaths per minute. The initial breathing period 306A may be determined based on feedback from a biosensor, such as the biosensor 212 of FIG. 2. In such an embodiment, the biosensor may be configured to measure the user's respiration. The biosensor may further be configured to detect whether the user is inhaling and exhaling.

In 404, a final breathing period 308A is selected. The final breathing period 308A is greater than the initial breathing period 306A. The final breathing period 308A may be selected by a user or subject, or may be preset or predetermined. An example of a final breathing period 308A is about a 10 second breathing period, corresponding to a final BrPM 308B about 6 breaths per minute.

In 406, a guiding stimulus (i.e., entrainment sounds) is output to a subject or user. The guiding stimulus may be output by a speaker, such as the speaker 208 of FIG. 2. In 408, the guiding stimulus is aligned with the initial breathing period 306A. The guiding stimulus is aligned with the initial breathing period 306A such that the guiding stimulus matches the rhythm or beat of the initial breathing period 306A. For example, an initial breathing period of about 4 seconds will have a quicker rhythm or beat than an initial breathing period of about 6 seconds.

In 410, the guiding stimulus is non-linearly altered to align with the final breathing period 308A over an interval of time. The interval of time is the total breathing entrainment period or total minutes of entrainment (i.e., the x-axis of graph 300). Altering the guiding stimulus comprises non-linearly decreasing the guided stimulus to align with the final breathing period 308A. The non-linear alterations of the guiding stimulus vary based on an amount of time the guiding stimulus has been output. In one embodiment, the beat or rhythm of the guiding stimulus is slowed or decreased to elongate or increase the breathing period of the user (i.e., decrease the BrPM of the user). While the breathing period 302 of the user is linearly altered, the BrPM 304 of the user is non-linearly altered with the guiding stimulus. In one embodiment, the breathing period may be non-linearly altered as well, if desired.

The non-linear alterations of the guiding stimulus may further vary based on an estimation of a current breathing pattern of the user. The current breathing pattern of the user may comprise at least one of a breathing period, breathing rate, and/or breathing architecture (i.e., exact inhale/exhale amplitude and/or length). The current breathing pattern of the subject may be estimated using a biometric sensor, such as the biosensor 212 of FIG. 2. The biosensor may be configured to detect whether the user is inhaling and exhaling, and to determine whether the sound output by the user's inhaling and exhaling is in or out of phase with the guiding stimulus.

The guiding stimulus may be a pre-produced sound or pre-produced soundtrack. Pre-produced sounds can be created at discrete breath periods. A pre-produced sound can be selected for playback if the slope of the breathing period is calculated to be within a predetermined tolerance. The resolution of the pre-produced experience may depend on the smallest gap in the discrete period values. Utilizing pre-produced sounds may require less computation power but may need more memory. Pre-produced sounds may also lead to a 'rougher' experience of the respiration period rise over time.

Additionally, the guiding stimulus may be dynamically generated. The guiding stimulus may be dynamically generated to get the finest resolution possible for a smoother entrainment experience. For example, the stimulus is dynamically generated mathematically by modulating attributes including the frequency, amplitude, duration, phase, envelope, and/or transients.

In another example, the dynamically generated stimulus comprises a limited set of pre-produced sounds (prerecorded or mathematically derived) sounds that are time-stretched to the desired period. The stimulus may be time-stretched using a vocoder. Dynamically generating the guiding stimulus may require less memory but may need more computational power. In an example, the set of pre-produced sounds have attributes that are modulated mathematically (e.g., the frequency, amplitude, duration, phase, envelope and/or transients).

To demonstrate the breathing period 302 linearly increasing while the BrPM 304 non-linearly decreases, several points 310A-320B on the graph 300 will be used as an example. The exemplary points 310A-320B are merely approximations, and may not be exact. A first breathing period 310A of about 4.8 seconds may be slowly increased to a second breathing period 312A of about 5.1 seconds over a time period of about 55 seconds, as shown in the graph 300. The guiding stimulus is non-linearly altered to correspondingly decrease the BrPM 304, as shown by corresponding point 310B at about 12.5 breaths per minute and point 312B at about 11.7 breaths per minute. Thus, while the breathing period 302 increases by about 0.3 seconds, the BrPM 304 decreased by about 0.8 breaths per minute.

Over another approximate 55 second time period, a third breathing period 314A of about 6 seconds is slowly increased to a fourth breathing period 316A of about 6.3 seconds. The guiding stimulus is non-linearly altered to correspondingly decrease the BrPM 304, as shown by corresponding point 314B at about 10.1 breaths per minute and point 316B at about 9.6 breaths per minute. Thus, while the breathing period 302 is increased by about 0.3 seconds, the BrPM 304 is decreased by about 0.5 breaths per minute.

Over yet another approximate 55 second time period, a fifth breathing rate 318A of about 8.6 seconds is increased to a sixth breathing rate 320A of about 8.9 seconds. Correspondingly, the guiding stimulus and BrPM 304 are non-linearly decreased from about 6.9 breaths per minute (shown by point 318B) to about 6.7 breaths per minute (shown by point 320B). Thus, while the breathing period 302 is increased by about 0.3 seconds, the BrPM 304 is decreased by about 0.2 breaths per minute.

As shown by the various points 310A-320B, as the minutes of entrainment progress, the breathing period 302 of the user increases at a constant linear rate while the BrPM 304 of the user non-linearly decreases in a non-linearly decay manner. The longer amount of time a user follows the entrainment sequence, the less the BrPM 304 decreases. As the user nears the final breathing period 308A, the breath rate per minute 304 of the user gradually lessens or elongates. This allows a user to minimize the amount of time spent at the higher BrPM, and enables the user to reach the final BrPM at a more natural and comfortable pace.

While the breathing period 302 is shown and described as linearly increasing, the breathing period 302 may also non-linearly increase. Having the breathing period non-linearly increase may be needed at the boundary conditions (beginning and end of the sequence) to smooth the transition between steady values. This may be accomplished by having a set of discrete a slope values that depend on the Period and/or t value(s) of Equation 1.

Utilizing a non-linear breathing entrainment method leads to a more comfortable entrainment experience for a user, as the non-linear entrainment minimizes sudden jumps and regulates a user's breathing in a more natural manner. The non-linear breathing entrainment may further enhance a user's ability to focus on their breathing with minimal distractions, leading to a more efficient way to achieve relaxation or sleep. Furthermore, the non-linear breathing entrainment may quicken the process of entrainment, as less time is spent in the higher breath per minute range than in a linear or step-wise approach. Additionally, the non-linear breathing entrainment may be utilized with a variety of audio systems or devices, as the non-linear breathing entrainment may be used with both open-loop and closed-loop systems.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. A method for breathing entrainment, comprising:
    selecting an initial breathing period, wherein a breathing period is an amount of time from a beginning of one inhale to an end of a next exhale;
    selecting a final breathing period, wherein the final breathing period is greater than the initial breathing period;

outputting, via at least one speaker of a wearable audio device, an audio signal to a user, wherein the audio signal is used to guide breathing of the user;

aligning the audio signal with the initial breathing period; and non-linearly altering, via a processor of the wearable audio device, the audio signal to align with the final breathing period over an interval of time by time-stretching the audio signal, wherein the non-linear alterations of the audio signal vary based on an amount of time the audio signal has been output, and wherein the audio signal is non-linearly altered an entire amount of time the audio signal is output.

2. The method of claim 1, wherein the non-linear alterations of the audio signal further vary based on an estimation of a current breathing pattern of the user.

3. The method of claim 2, wherein the current breathing pattern of the user is estimated using a biometric sensor.

4. The method of claim 1, wherein the audio signal is one of: a pre-produced sound, a pre-produced soundtrack, or dynamically generated.

5. The method of claim 1, wherein the final breathing period is one of: preset, user-selected, or based on input collected using at least one biometric sensor.

6. The method of claim 1, wherein the initial breathing period is user-selected.

7. A wearable audio device, comprising:

at least one speaker configured to output an audio signal to a user, wherein the audio signal is used to guide breathing of the user; and a processor, the processor configured to:

select an initial breathing period, wherein a breathing period is an amount of time from a beginning of one inhale to an end of a next exhale;

select a final breathing period, wherein the final breathing period is greater than the initial breathing period;

align the audio signal with the initial breathing period; and non-linearly alter the audio signal to align with the final breathing period over an interval of time by time-stretching the audio signal, wherein the non-linear alterations of the audio signal vary based on an amount of time the audio signal has been output, and wherein the audio signal is non-linearly altered an entire amount of time the audio signal is output.

8. The wearable audio device of claim 7, wherein the non-linear alterations of the audio signal further vary based on an estimation of a current breathing pattern of the user.

9. The wearable audio device of claim 8, wherein the current breathing pattern of the user is estimated using a biometric sensor.

10. The wearable audio device of claim 7, wherein the audio signal is one of: a pre-produced sound, a pre-produced soundtrack, or dynamically generated.

11. The wearable audio device of claim 7, wherein the final breathing period is one of: preset, user-selected, or based on input collected using at least one biometric sensor.

12. The wearable audio device of claim 7, wherein the initial breathing period is user-selected.

13. An audio system, comprising:

at least one speaker configured to output an audio signal to a user, wherein the audio signal is used to guide breathing of the user; and a processor, the processor configured to:

select an initial breathing period, wherein a breathing period is an amount of time from a beginning of one inhale to an end of a next exhale;

select a final breathing period, wherein the final breathing period is greater than the initial breathing period;

align the audio signal with the initial breathing period; and non-linearly alter the audio signal to align with the final breathing period over an interval of time by time-stretching the audio signal, wherein the non-linear alterations of the audio signal vary based on an amount of time the audio signal has been output, and wherein the audio signal is non-linearly altered an entire amount of time the audio signal is output.

14. The audio system of claim 13, wherein the non-linear alterations of the audio signal further vary based on an estimation of a current breathing pattern of the user.

15. The audio system of claim 14, wherein the current breathing pattern of the user is estimated using a biometric sensor.

16. The audio system of claim 13, wherein the audio signal is one of: a pre-produced sound, a pre-produced soundtrack, or dynamically generated.

17. The audio system of claim 13, wherein the final breathing period is one of: preset, user-selected, or based on input collected using at least one biometric sensor, and wherein the initial breathing period is user-selected.

18. The method of claim 1, wherein the non-linear alterations of the audio signal are based on a breath rate per minute of the user, the breath rate per minute being the inverse of the breathing period.

19. The wearable audio device of claim 7, wherein the non-linear alterations of the audio signal are based on a breath rate per minute of the user, the breath rate per minute being the inverse of the breathing period.

20. The audio system of claim 13, wherein the non-linear alterations of the audio signal are based on a breath rate per minute of the user, the breath rate per minute being the inverse of the breathing period.

* * * * *